(12) United States Patent
Wixforth

(10) Patent No.: US 6,777,245 B2
(45) Date of Patent: Aug. 17, 2004

(54) PROCESS FOR MANIPULATION OF SMALL QUANTITIES OF MATTER

(75) Inventor: Achim Wixforth, Munich (DE)

(73) Assignee: Advalytix AG, Munich (DE)

(*) Notice: Subject to any disclaimer, the term of this patent is extended or adjusted under 35 U.S.C. 154(b) by 402 days.

(21) Appl. No.: 09/766,677

(22) Filed: Jan. 23, 2001

(65) Prior Publication Data

US 2001/0055529 A1 Dec. 27, 2001

(30) Foreign Application Priority Data

Jun. 9, 2000 (DE) ........................................ 100 28 625
Nov. 9, 2000 (DE) ........................................ 100 55 318

(51) Int. Cl.⁷ .............................................. G01N 1/10
(52) U.S. Cl. ..................... 436/180; 310/313; 422/73; 422/82; 422/100; 422/101; 422/110
(58) Field of Search ................... 436/180, 74, 177; 422/73, 82, 100, 101, 110, 99, 81, 68.1; 310/313

(56) References Cited

U.S. PATENT DOCUMENTS

| | | | |
|---|---|---|---|
| 4,280,823 A | 7/1981 | Szonntagh | |
| 5,006,749 A | 4/1991 | White | 310/323 |
| 5,674,742 A | 10/1997 | Northrup et al. | 435/286.5 |
| 6,010,316 A | 1/2000 | Haller et al. | 417/322 |

FOREIGN PATENT DOCUMENTS

| | | |
|---|---|---|
| DE | 196 09 472 A1 | 9/1997 |
| DE | 19736641 | 3/1999 |
| FR | 2 757 590 A 1 | 6/1998 |
| JP | 58-059613 | 4/1983 |
| JP | 06 050974 | 2/1994 |
| JP | 10-327590 | 12/1998 |
| WO | WO 99/03684 | 1/1999 |

OTHER PUBLICATIONS

Fu et al., A microfabricated fluorescence–activated cell sorter, Nature Biotechnology, vol. 17, 1999, p1109–1111.
Müller, Lab–on–a–Chip–Technologie– Revolution im (bio–) analytischen Labor, Laborwelt, 2000, p36–38.
Uchida et al.; Investigation of Acoustic Streaming Excited by Surface Waves; 1995 IEEE Ultrasonics Symposium; pp 1081–1084.
Liquid Streaming and Droplet Formation Caused by Leaky Rayleigh Waves, S. Shiokawa et al, 1989 Ultrasonics Symposium, 1989 IEEE, pp. 643–646.

*Primary Examiner*—Jill Warden
*Assistant Examiner*—Sam P. Siefke
(74) *Attorney, Agent, or Firm*—Jacobson Holman PLLC (57) ABSTRACT

A process for specific and direct manipulation of small quantities of matter on solid-body surfaces, in which surface waves are generated with at least one surface-wave generator and the impulse of one or more surface waves is made to interact with at least one quantity of matter, in order to cause a movement in a desired direction.

60 Claims, 7 Drawing Sheets

PROCESS FOR MANIPULATION OF SMALL QUANTITIES OF MATTER

BACKGROUND OF THE INVENTION

1. Field of the Invention

The invention concerns a device and a process for directed and specific manipulation of small quantities of matter on the surface of a solid body and use thereof.

2. Description of the Related Art

Movement of small quantities of matter is performed at this point in time primarily in the field of liquids (microfluids). Thus movement of small quantities of liquids (and at the same time suspended particles contained in them, such as biological cells) on a chip has already been used in biology (Anne Y. Fu et al., *Nature Biotechnology* 17 (1999), pages 1109f). To move small quantities of matter, conventional pump systems (including miniaturized pumps) are used on the one hand, that move defined quantities of liquids along defined channels by structuring solid-body surfaces. These conventional pump systems are based essentially on miniaturization of known functional units, which are driven by purely mechanical or piezoelectric actuators. In this, methods of micromechanics are used, among others, based on significant miniaturization of known pump mechanisms or known hydraulic and hydrodynamic functional blocks, such as valves, turbines, nozzles, etc. Another type of liquid transport that has arisen recently is based on utilization of electrokinetic processes, in which an electric field causes movement of a liquid along a defined channel (O. Müller, Laborwelt 1/2000, pages 26 though 38). Movement of small liquid quantities by impulse transfer of a longitudinal volume sound wave on a liquid is known from U.S. Pat. No. 5,674,742 and from U.S. Pat. No. 6,010,316.

In electroosmotic processes, the speed of the quantities of matter to be moved depends on the channel width, as a rule. In addition, the channel must be completely filled, in principle. Also, high field strengths are required to transport small quantities of liquid, which lead, in addition to undesired electrochemical and electrobiological effects, also to an unavoidable joule heating of the quantities of matter to be moved, which can, among other things, affect the functionality of the carrier material.

SUMMARY OF THE INVENTION

The task of the present invention is to provide a device and a process, with the help of which specific manipulation and movement of the smallest quantities of matter on and along the surface of a solid body, in which the movement of the smallest quantities of matter is possible without moving parts and makes cost-favorable and simple production and use possible.

This task is accomplished by a process and device for specific and direct manipulation of small quantities of matter on solid-body surfaces in which, with the aid of one or more acoustic surface waves, an impulse is generated along the solid-body surface, with the surface wave being generated with a surface-wave generator. The impulse is made to interact with at least one quantity of matter in order to cause movement on the surface in a desired direction.

In the process according to the invention, surface waves are generated with the aid of at least one surface-wave generating device, the impulse of which is made to interact with at least one quantity of matter, in order to cause movement in a desired direction. The device according to the invention also has at least one device for generating surface waves on a solid-body surface in at least one direction of spreading and an interaction region, in which the quantity of matter can interact with the at least one surface wave, in order to cause movement of the quantity of matter through an impulse transfer by the surface wave or surface waves.

With the process according to the invention and the device according to the invention, the smallest quantities of matter on the surface of a solid body can be moved or manipulated specifically by means of acoustic surface waves. Here, the concept "matter" includes gases, liquids, and solid substances, but also biological systems, such as cells, macromolecules, and genetic material, as well as small particles, such as chemical reagents or mixtures, solutions, or dispersions of these substances. At least one acoustic surface wave is generated on the surface of the solid body. Through the interaction of small particles, liquids, or gases with the periodic mechanical deformation of the surface, or also through interaction with the electric fields accompanying the wave, these particles, liquids, or gases are moved specifically. Here, the amount and direction of each speed can be set in advance externally. Transport of the matter on the surface of the solid body along a path that can be selected freely and set specifically is thus caused by an impulse transfer between an acoustic surface wave and the small quantity of matter to be transported. Manipulation or movement of the small quantities of matter on the surface of the solid body takes place without direct contact between the actual "pump" and the matter to be transported, since the displacement of the matter is caused by the impulse transfer alone, which occurs, e.g., through mechanical deformation of the solid-body surface or also through electric forces, transmitted through the piezoelectric fields accompanying the surface wave. In addition, at at least one point on the solid-body surface, a corresponding sound converter or a surface-wave generator is prepared, through which a high-frequency acoustic surface wave can be excited along the surface of the solid body.

Matter transport through impulse transfer from a surface wave permits high current and process speeds with comparatively small electric field strengths up to the speed of sound for surface waves on the corresponding substrate. Moreover, the process presented can be scaled over broad ranges, since the speed of the quantity of matter to be moved does not depend on the channel width, as it does, e.g., in the electroosmotic process. In contrast to, e.g., the electroosmotic transport process, no high field strengths are needed for transport that could possibly lead to undesired electrophysical or electrochemical reactions. The small quantities of matter to be transported are located, disregarding any high-frequency alternating field that may be present accompanying the surface wave, in a field-free space. Especially for biological systems, such as cells, damaging effects of high electric fields are thus avoided. The method of functioning of the pump mechanism is independent of the type and properties of a transport or buffer liquid that may be used. In addition, with the process according to the invention, undesired joule heating is avoided.

Since both the direction of the effectively acting surface wave or surface waves on the solid-body surface, as well as their position and amplitude can be set as desired and separately, it is possible to set the transport speed specifically with respect to amount and direction. Thus it is possible to define complex transport segments and paths for small quantities of matter on the solid-body surface.

The surface wave can be generated either continuously or in pulse form.

Finally, it is not necessary, e.g. with closed fluid volumes, to irradiate the entire volume with the surface wave, since because of the incompressibility of liquids, driving a small partial volume is sufficient to move the entire volume.

Another advantage of the device according to the invention is the possibility of moving individual drops, e.g. of a liquid or a buffer solution, forward. Because of surface tension, drops of this kind do not run away from each other. Small quantities of matter can thus be transported without a surrounding column of liquid.

Finally, the process according to the invention and the device according to the invention makes a very directed control of the movement mechanism possible. The surface waves runs laterally, because of the crystal properties of the substrate, * to their being generated on the surface only slightly apart from each other. In this way, a very definite effect of the surface wave on the small quantity of matter is possible, even when the direction in which the surface waves are generated is not in the immediate neighborhood of the small quantity of matter to be moved.

With the device according to the invention, construction of a "lab on the chip" is possible. Here, a "chip," such as is known, e.g., from electronics, serves as a solid-body surface or substrate. Various devices according to the invention can be combined for various purposes. Finally, one or more analysis stations can also be provided on the same chip surface, in which the quantity of matter is made to interact with an external measurement quantity, e.g. a local illumination, a local heating, a local magnetic field, an electric field, or, e.g., a local mechanical load.

In this case, the device according to the invention can be produced in a simple manner and the process according to the invention can be implemented easily.

Advantageous embodiments of the invention are objects of the subclaims.

All materials can be considered as solid bodies on which an acoustic surface wave can be generated. Especially suitable, because of their functionality, are, e.g., semiconductor surfaces.

Acoustic surface waves can be stimulated in an especially simple manner, in which case the use of piezoelectric solid-body surfaces is advantageous.

The movement device for a quantity of matter can result directly from the impulse direction of the surface wave or the impulse direction of the vector sum of the impulses of individual surface waves. It is possible, however, to provide the solid-body surface with predetermined defined trajectories, along which the quantity of matter will move. In predetermined trajectories of this kind, the direction of movement is determined by the direction of the trajectory, so that a slight angular error in the direction of the impulses of the surface waves does not damage the desired direction.

Trajectories of this kind can be achieved by grooves, barriers, lithographic definition of channels, or modulation of the wetting properties of the solid-body surface. Such structures can easily be applied to solid-body surfaces, e.g. through lithographic processes, which are well known from planar technology. By combining several regions defined in this way on the solid-body surfaces, "conducting paths," mixing chambers, branches, or networks can easily be produced. The definition of a complex network of "conducting paths" made in this way for matter transport on the surface of a solid body makes it possible to prepare completely functional units for physical, chemical, or biological manipulation of matter on the surface of the solid body.

In a special embodiment, functionalization of the solid-body surface is achieved by modulation of the wetting properties of the solid-body surface. This can occur, e.g., by defining hydrophobic and hydrophilic regions on the surface of the solid body, e.g. by direct coating of parts of the solid-body surfaces or by micro- or nanostructuring of certain regions of the surface of the solid body. The shape, position, and breadth of "conducting paths" defined in this way can be set directly, for example by lithographic techniques. Combining these "conducting paths" with regions of the solid body that have been functionalized in a similar way, which then serve as reservoirs, mixing chambers, analysis stations, or sensitized regions for sensor applications, permits a large band width of possible applications of the present invention as a "lab on a chip." All process steps are based on known processes of semiconductor technology, so that a specific adaptation of the chip layout can be made for a special problem or an application in a rapid and cost-favorable manner.

Definition of "conducting paths" for liquids by modulation of the wetting properties of an otherwise planar surface avoids the etching of grooves. This also automatically avoids a blockage of small channels, and a cleaning of the solid-body surface that may be needed is very simple.

Because of the planar surface, sticking of the matter to be moved at corners or edges is excluded. In addition, layers could be obtained in a simple manner with known coating techniques for modulating the wetting properties.

Providing strips of relevant surface regions according to the invention with surface waves also generates an inherent cleaning effect, which simplifies additional cleaning or makes it superfluous.

The wetting behavior of "conducting paths" produced in planar technology for liquids based on modulation of the wetting properties of the solid-body surface in addition to depending on to special functionalization of the surface (coating, mechanical handling, changing the composition) itself, is also sensitive to the volumes to be transported. In this way it can be achieved that certain regions along a conducting path are wetted or not along a conducting path when excess liquids are introduced. By this means, e.g. self-organizing valve functions can be realized.

With this, the quantity of matter to be moved can be kept in either hydrophobic or hydrophilic and either lipophobic or lipophilic regions according to their adhesion properties.

In another embodiment, modulation of the wetting properties is achieved by silanization of a portion of the solid-body surface. To generate a "conducting path" for an aqueous solution, the surrounding region can be made hydrophobic by, e.g. silanization.

Advantageously, the acoustic surfaces are generated by electric stimulation. A simple possibility for this is offered by interdigital converters, so-called interdigital transducers. In the simplest embodiment, these consist of at least two metal structures the mesh in the manner of combs, applied in at least one planar-technology process to a substrate surface. If a high-frequency alternating-voltage signal is applied to such an interdigital structure, then a crystal deformation results according to the inverse piezoelectric effect, which has the spatial periodicity of the interdigital converter and the time periodicity of the high-frequency alternating voltage. To the extent that the applied high-frequency alternating-voltage signal is applied in resonance with the speed of sound on the surface involved, then an acoustic surface wave spreads out perpendicularly to the axis of the converter. The corresponding resonance condition is $f = v/\lambda$, where f is the frequency of the applied alternating field, v is the speed of sound of the surface waves, and $\lambda$ is the spatial periodicity of the interdigital converter.

If the acoustic surfaces are generated by means of the piezoelectric effect, then the impulse transfer between the at least one acoustic surface wave and the at least one quantity of matter can be transmitted through the electric fields accompanying the waves in the piezoelectric substrate by transmitting electric forces to charged or polarizable matter. In another embodiment of the process, the accompanying mechanical deformation of the solid-body surface is used to transfer for impulse transfer to the quantity of matter.

The piezoelectric effect can be generated in the substrate itself if a piezoelectric substrate is used. On the other hand, the piezoelectric effect can also be used in a piezoelectric layer on the substrate surface. The piezoelectric layer can be selected in such a way that it has different wetting properties than the rest of the substrate surface. In this way, a modulation of the wetting properties can be used at the same time* to generate the piezoelectric effect to form "conducting paths".

Preferred embodiments include unweighted converters, weighted converters, monodirectionally radiating converters, focusing converters, and converters for multi-frequency operation. Matter transport then occurs along the direction of spreading of the surface waves. By superimposition of several surface waves, a resultant total impulse can be set whereby the spreading of the quantity of matter does not necessarily have to occur parallel to the spreading direction of the surface waves. In addition, the frequency, amplitude, and also the phase position can be set directly with respect to another wave, in order thus to generate complex interference and superimposition patters. Thus both the quantity and also the direction of the velocity vector can be set directly for the matter transport within broad limits.

Interdigital converters can also be generated very simply with known planar-technology methods on surface-body surfaces. The represent a well-defined purely electric interface between the device and possible external guidance and control electronics. It is likewise conceivable that the necessary surface waves or pulse sequences can be controlled through the wireless radiation of a high-frequency alternating voltage. For this, e.g. an antenna device can be provided.

Converters with constant distances between fingers can be used as interdigital converters. The a uniform surface wave is sent through the entire width of the interdigital converter over the surface, when a corresponding frequency is applied.

If several interdigital converters are provided on the surface that can move or manipulate the quantity of matter in different directions, it can be achieved through suitable selection of the distances between fingers in each case that the various interdigital converters come into resonance at different frequencies. Thus the frequency of each interdigital converter can be selected and thereby the quantity of matter can be manipulated in the desired manner.

In an advantageous embodiment, it is provided that at least one interdigital converter is used with a non-constant distance between fingers for generation of surface waves of different frequencies. In this case, the surface waves are generated only at the place where the resonance condition is satisfied. Different frequencies thus lead to a stimulation of surface waves at different points of the interdigital converter. The non-constant distance between the meshing fingers of the interdigital converter can be changed, e.g. stepwise. Especially simple, however, is a so-called "tapered" interdigital transducer. Here, the distance between the fingers of the interdigital converter changes continuously, e.g. linearly. As the frequency increases, the place of stimulation moves continuously along the interdigital converter. Thus the region in which the surface wave spreads can be set very precisely and a very local impulse transfer to a small quantity of matter is possible. Likes, various quantities of matter can be controlled selectively by choosing the frequency, if the axis of the interdigital transducer is kept divided, e.g. along the interdigital transducer.

By selecting complex combinations or sequences of the operating frequency, a multiplexing or switching of matter currents is possible. With only one high-frequency source that controls the transducer with non-constant distances between fingers, a number of possible paths can be programmed and set, along which acoustic surface waves move the smallest quantities of matter.

Thus specific control of the smallest quantities of matter along predetermined paths is possible using a single device, without moving parts. Thus the device can be set completely through the operating frequency and also the amplitude of the high-frequency alternating voltage applied to the transducer. With several interdigital transducers of the type mentioned, it is possible to generate complex wave fields by manipulation of the smallest quantities of matter along the surface of the substrate involved.

Here too it is possible to stimulate the generation of surface waves by wireless irradiation of a high-frequency field of a definite frequency. By selecting the frequency, the place where the surface waves are generated can be specified very precisely.

The process according to the invention for manipulating or moving a quantity of matter can be used to divide a quantity of matter into two parts by irradiating an acoustic surface wave. In this case, an acoustic surface wave is sent, e.g., to a quantity of matter at rest. By selecting parameters appropriately, parts of the quantity of matter then move away from each other. It can likewise be provided that a moving quantity of matter, moved e.g. by a device according to the invention, is divided with a surface wave sent from the side and thus divided into two subquantities.

Another embodiment of the process according to the invention makes a mixing possible, in which surface waves are sent from various directions to at least one quantity of matter. By this means, the quantity of matter can be changed in motion without changing its overall position.

In order to mix two drops of liquid, they can be moved directly toward each other by an embodiment of the process according to the invention. Two surface-wave generators, the radiating characteristics of which consist of at least two parts running at an angle of 180 degrees from each other, generate surface waves that cancel each other's effects under normal circumstances. If, however, the surface wave in one of these generating directions encounters a first small quantity of matter, e.g. a drop of liquid, then on the one hand it transfers an impulse to it and on the other hand it is attenuated. If it then encounters another small quantity of matter, it is already weakened in its effect. Similarly, the surface wave generated by the other surface-wave generator transfers an impulse to the other quantity of matter and is attenuated. The effect of the surface waves in opposite surface-wave generating directions is thus stronger at the place of the quantity of matter than is nearer to each surface-wave generator. Thus two small quantities of matter, e.g. drops of liquids, can be driven directly toward each other in order to be mixed or for purposes of a reaction.

In another embodiment according to the invention, a surface wave is sent approximately tangentially to the at least one small quantity of matter, so that it is caused to rotate.

A device according to the invention can also include e.g. a defined trajectory with an essentially round region, whereby the at least one generating direction for surface waves is arranged in such a way that a surface wave can be generated in a direction tangential to this round region. A centrifuge can be generated in this way.

In a further development of the process according to the invention, the quantity of matter is analyzed inside at least one region of the solid-body surface with respect to a physical, chemical, or biological characteristics. This can take place during the application of the surface wave to generate a movement, or the process according to the invention can be used to transport the quantity of matter to an analysis station.

A process designed in this manner offers the advantage that both the movement and the analysis of the quantity of matter are possible on one "chip."

For example, the at least one quantity of matter can be separated from the rest of the quantity of matter, either before or after the analysis, e.g. by irradiation of a surface wave.

A separation can also be achieved with a single surface wave. If a surface wave is sent to a small quantity of matter, e.g. a quantity of liquid, then the quantity of matter is placed in motion by transfer of an impulse to a part of the total quantity of matter, because of the surface tension and the incompressibility of the liquid. If, however, a surface wave is selected with a strength whose impulse can overcome the surface tension, then a part of the quantity of matter can be separated and moved forward by the impulse transfer from the surface wave.

Finally, a protecting layer can be applied to a device according to the invention, the thickness of which is less than the typical penetration depth of a surface wave. Such a protective layer is important when materials should be manipulated that would be damaged on the piezoelectric substrate used or the piezoelectric region of the substrate. Thus, e.g., a biological molecule would be damaged on a piezoelectric substrate of gallium arsenide. If the layer is thinner than the typical penetration depth of a surface wave, i.e. about a wavelength, then the functionality of the piezoelectric surface does not suffer or suffers only a little by the application of a protective layer. Alternatively, a substrate can be used of a material with a desired surface chemistry, even if this material is not piezoelectric. Then the surface is coated in the desired regions with a piezoelectric material, e.g. zinc oxide. In this case, it may be sufficient, e.g. when an electric-stimulation mechanism is used, to apply the piezoelectric coating material only in the region of the surface in which the surface-wave generating direction is located. There, the surface wave is then generated by the piezoelectric effect, and it cannot move forward in the non-piezoelectric substrate.

Finally, a piezoelectric coating can also be used in selected regions of the surface to modulate the wetting properties.

A protective layer can be made e.g. of quartz. Such a quartz layer is harmless, e.g. for biological molecules.

Analysis of e.g. size, masse, optical, magnetic, electric, and/or dielectric properties can likewise by performed with the aid of surface waves. In addition, the quantity of matter can be irradiated with a surface wave and the effect of the quantity of matter on the surface wave can be studied.

It is likewise possible that the quantity of matter can be modified in at least one region of the solid-body surface in which it applied, e.g. with the aid of surface waves, by chemical, physical, or biological processes. This can be achieved e.g. with appropriate functionalizing of a region of the solid-body surface in regard to physical, chemical, or biological properties.

It is especially advantageous for the quantity of matter to be immobilized reversibly and temporarily on at least one region of the solid-body surface, by modulation or coating of this region, for analysis purposes or modification purposes, by chemisorption or physisorption. This is achieved, e.g., by an appropriate functionalization of the solid-body surface, when e.g. it is rougher than the surroundings or has different wetting properties.

The process according to the invention can also be used to bring at least two quantities of matter into contact in at least one region of the solid-body surface by specific or directed movement for the purpose of at least one physical, chemical, biological reaction. This special embodiment of the process according to the invention makes possible a reaction between very small quantities of matter. Acoustic surface waves are used to transport the individual quantities of matter toward each other, bring them into contact, and possibly to mix them. If necessary, surface waves can then be used to strengthen or stop the reaction between the two quantities of matter used.

In an embodiment of the process according to the invention, an external supply reservoir or an external receiving reservoir can be connected with the aid of a defined trajectory on the device, in order to transport the quantity of matter into the device or out of the device.

A supply reservoir or a receiving reservoir can also be provided on the solid-body surface itself, in order to deliver or collect the quantity of matter.

Such a reservoir can be formed by appropriate functionalization of the surface, e.g. by lithographically defined grooves or barriers. It is likewise conceivable to change a solid-body surface in its wetting properties so that the quantity of matter stays in it preferentially. An appropriate modulation of the wetting properties can be generated in a similar manner as modulation of the wetting properties is achieved for the embodiment with defined trajectories.

In one embodiment of the process according to the invention, a region of the solid-body surface is provided with a device for local warming. Such a device makes it possible for a quantity of matter to be moved with the aid of acoustic surfaces* to or through a heated region, in order, e.g. to promote a reaction.

The device according to the invention or the process according to the invention can be used wherever small quantities of matter should be moved or manipulated on a solid-body surface. This is conceivable in liquids, gases, solid bodies, or combinations, mixtures, and/or dispersions. The process according to the invention or the device according to the invention can be used advantageously for analysis, synthesis, separation, mixing, proportioning, or centrifuging of a small quantity of matter.

BRIEF DESCRIPTION OF THE DRAWINGS

Various embodiments of the device according to the invention or the process according to the invention will be explained in more detail with reference to the attached diagrams.

Here.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
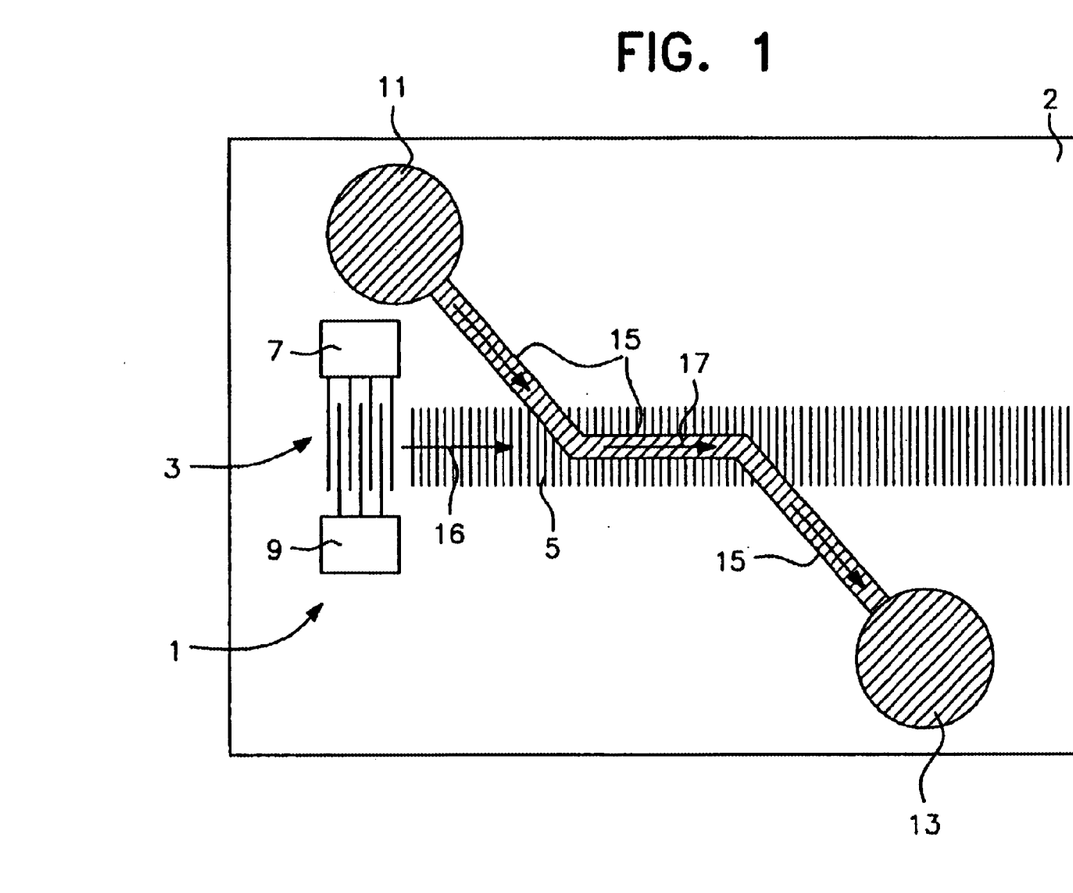
FIG. 1 shows a top view of a first embodiment of a device according to the invention, in a schematic representation.

If FIG. 1, 1 shows an interdigital transducer. The number of meshing metallic finger electrodes 3 is very much higher in real embodiments and distances between them are much smaller, corresponding approximately to the wavelength of the surface waves to be generated. 7 and 9 denote electrodes for connection of a high-frequency alternating voltage. The interdigital transducer is generated with the aid of lithographic techniques in known ways on the surface of the chip 2. The chip 2 is a piezoelectric substrate. The resonance frequency of the interdigital transducer 1 can be calculated from the speed of sound on the piezoelectric substrate 2 and the distance between fingers $\lambda$ as $f=v/\lambda$. When an alternating field with this frequency is applied, a surface wave is generated that spreads in the direction perpendicular to the fingers 3 of the interdigital transducer 1. A region covered by the surface wave is denoted by 5. In the schematic representation of FIG. 1, the region 5 covered by the surface wave is shown, for clarity, not up to the generating transducer 1, but only in the region of interest, in which it covers the conducting paths 15 with a surface wave. This also applies to the following FIGS. 2 through 4.

Typical materials that can be used as solid bodies include, e.g., lithium niobate or quartz. Zinc oxide can be used as a piezoelectric coating material. Typical frequencies are a few hundred MHz, in which case typical distances between fingers of the interdigital transducer are a few microns.

15 denotes a "conducting path" for the quantity of matter. This conducting path can be defined e.g. lithographically, and it can have different wetting properties from the surrounding solid-body surface. For example, this conducting path can include a coating material hydrophilic material that is hydrophilic with respect to the rest of the surface. According to the quantity of matter to be manipulated, a lipophobic, lipophilic, hydrophobic, or hydrophilic coating of the "conducting path" or the surroundings can be selected.

11 denotes a likewise modified surface region, which serves as a supply reservoir. 13 denotes a corresponding receiving reservoir, which likewise has appropriately modified surface characteristics. The surface-wetting properties are changed in this case so that the quantity of matter stays preferentially in regions 11, 15, and 13.

17 denotes the motion of the quantity of matter that can be achieved with the aid of the irradiated surface wave radiated by the transducer 1 in direction 16.

The method of operation is as follows:

A quantity of matter, e.g. a liquid, is applied to region 11 of the chip 2. Part of the liquid is spread as far as the region of the surface-wave path 5. At the time when a movement of the liquid is desired, a high-frequency signal is applied to the electrodes 7, 9 of the interdigital transducer 1. The surface wave spreads out perpendicularly to the fingers 3 of the interdigital transducer. This transmits an impulse to the matter in region 15 and leads to a motion in direction 17. Since the material stays preferentially in the regions with appropriately modified surface-wetting properties 11, 15, 13, the quantity of matter moves correspondingly in the direction of the receiving reservoir 13. In this way, matter from the supply reservoir 11 is "pumped" into the supply* reservoir 13. There, e.g. an analysis can take place. E.g. a local optical detection, application of a local magnetic field or a local electric field, a mechanical load, or a local heating is possible. Likewise, region 13 can have a chemically or physically modified surface, so that a quantity of matter moved to it undergoes a reaction.

In the course of the process presented above, a surface wave is selected with a strength that cause an impulse to be transferred to the quantity of matter that cannot overcome the surface tension. In this way, the matter is led completely from reservoir 11 to reservoir 13.

If a surface wave of greater strength is selected, a smaller portion of the material is separated. The stronger surface wave meets the quantity of matter in region 5. The quantity of matter encountered by the impulse of the stronger surface wave separates from the rest of the volume of material, since the surface tension is overcome by the greater amount of the impulse. In this way, a small drop-shaped quantity of matter is separated and transported to reservoir 13. The strength of the surface wave necessary for this application can be determined is a simple preliminary experiment.

Typically, quantities of matter on the order of picoliters or milliliters can be moved by modification of the "conducting paths" generated by modification of the surface tension with a width on the order of 10 microns.

In an embodiment not shown in the figures, there is, e.g. in region 13 of FIG. 1, a coating for local heating of the material found on it, e.g. to accelerate or promote a reaction. Such a coating can be, e.g., a high-resistance metal layer, heated by means of an electric current.

Figure 2:
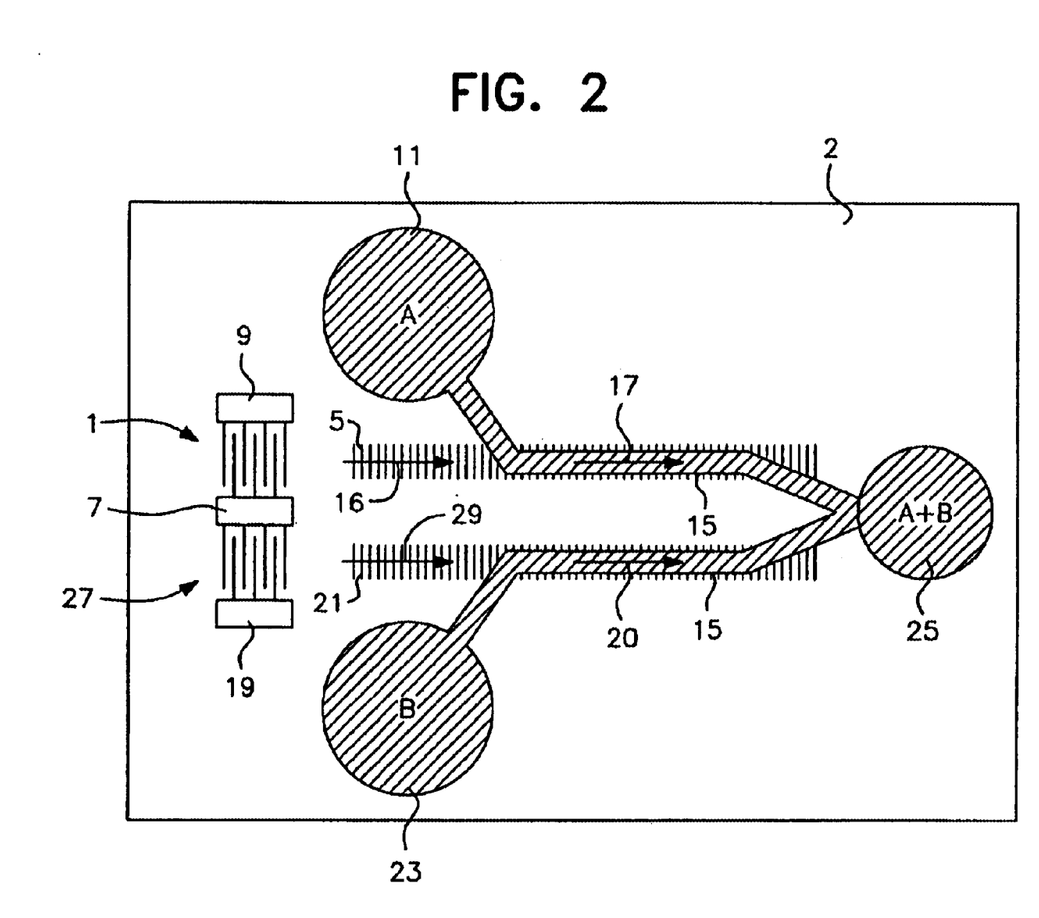
FIG. 2 shows a top view of a second embodiment of a device according to the invention, in a schematic representation.

FIG. 2 shows the embodiment of a device according to the invention as a mixing chamber. The same reference numbers denote the same elements.

A second supply reservoir 23 is provided, which is connected through another conducting path to a mixing region 25. The supply regions 11, 23, the conducting path 15, and the mixing region 25 are formed by appropriate modulation of the wetting properties of the surface of the chip 2. In addition to the first interdigital transducer 1, there is a second interdigital transducer 27. The transducers have electrode 7 in common, and 19 denotes the second electrode of the second transducer 27. When an appropriate frequency is applied, transducer 27 generates a surface wave, which is calculated according to the above formula, in region 5 in direction 16. When a quantity of liquid A is located in the supply region 11, there is a quantity of liquid B, in supply region 23, of which part of each has spread into the conducting path 15. When a surface wave is irradiated from transducer 1 and/or 27, an impulse is generated on quantities of matter A and/or B in direction 17 and/or 20, respectively. The individual quantities of matter on the pretreated conducting path 15 move in the direction of the mixing region 25, where they are combined into the mixture A+B.

If the interdigital transducers 1 and 27 have different distances between fingers, then it can be achieved, through selection of the frequency, that only one of the transducers generates a surface wave at a time. Thus the quantities of matter can be moved from supply regions 11 or 23 simultaneously, one after another, or in alternation. Since the amplitudes of the surface waves can be set individually and a pulse operation is also possible, well-defined smallest amounts of liquid can be made to react or mixed by the ultrasound of the surface waves. Thus parallel independent analyses or syntheses are possible on a chip with only one control device. The surface waves of the interdigital transducers 1 and 27 also promote mixing of individual quantities of matter A and B in the mixing region 25.

Figure 3:
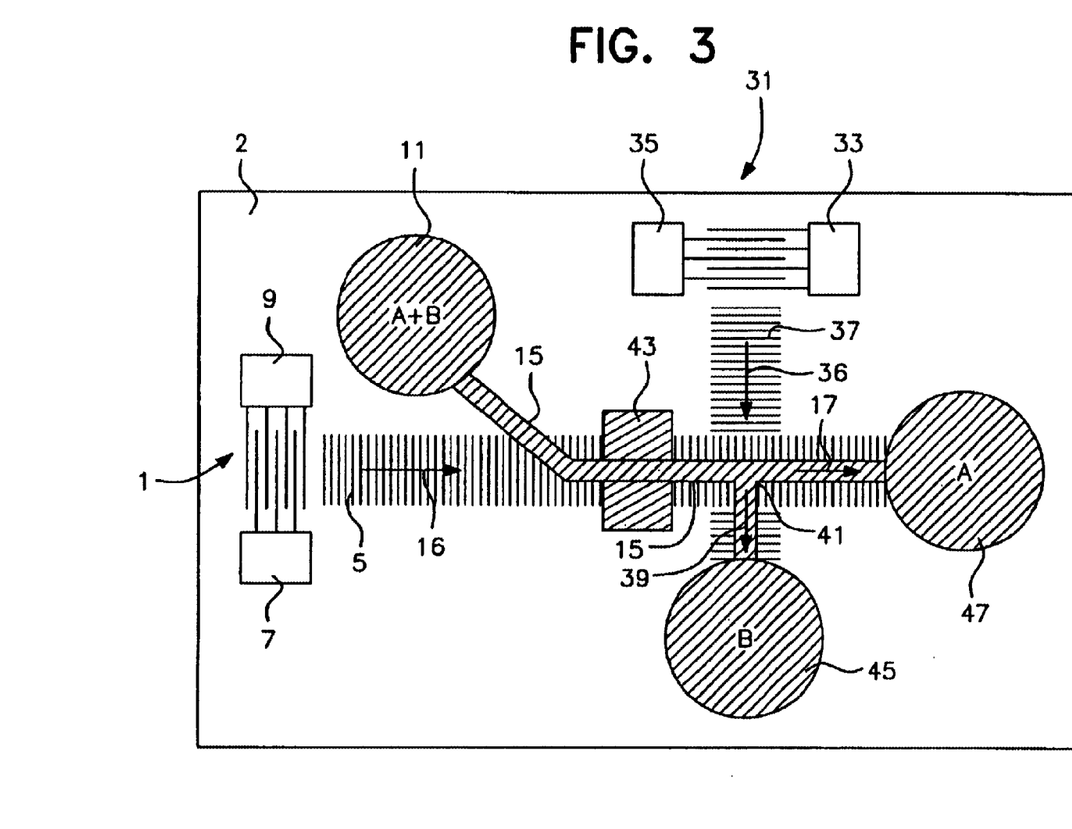
FIG. 3 shows a top view of a third embodiment of a device according to the invention, in a schematic representation.

FIG. 3 shows an embodiment that can serve for sorting suspended particles in a liquid (for example biological cells) with respect to a particular property.

A surface-wave path 5 can be irradiated in turn with an interdigital transducer 1. Another region 37 can be provided with a second transducer 31 with electrodes 33 and 35 and covered by a surface wave. For selective control of the two interdigital transducers 1, 31, these can be provided with different distances between fingers, so that when irradiated with a particular frequency only one of the interdigital transducers generates a surface wave. Whereas interdigital transducer 1 generates a surface wave in direction 16, interdigital transducer 31 generates a surface wave in direction 36, essentially perpendicular to the first surface wave. A supply reservoir 11 is connected to receiving reservoirs 45 and/or 47 by the conducting paths 15 shown, which can be obtained in turn by modulation of the wetting properties of the surface of the chip 2, which are connected by the conducting paths to the crossing region 41, which can be covered by a surface wave from both interdigital transducers 1, 31. 43 denotes an analysis region.

Reservoir 11 contains, for example, a buffer liquid, in which there are, e.g., two types of biological cells A and B. An interdigital transducer 1 generates an acoustic surface wave in direction 16 when a suitable high-frequency voltage is applied, which transports the liquid, together with the cells in it, from reservoir 11 in the direction of the analysis region 43 by an impulse transfer, as in the embodiments of FIGS. 1 and 2. This in turn takes place by the surface wave in direction 16 meeting the matter material, which has already entered the conducting path from the supply container 11. Because of the surface tension of the liquid, the liquid is drawn out of the reservoir 11 when a surface wave appears on the conducting path 15, in which matter already is found. In the analysis region 43, for example, cells of type B are identified unambiguously. This takes place, for example, through a known fluorescence-marker analysis, in which cell type B is marked with a fluorescent marker and is stimulated to fluoresce by illumination in region 43. The signal from the optical detector, not shown in FIG. 3, is used to address an alternating-voltage source, which is connected to interdigital transducer 31. This alternating voltage is then applied to interdigital transducer 31, which immediately generates a surface-wave impulse in direction 36. This surface-wave impulse meets the matter in the crossing region 41, and the matter moves along the conducting path 15. According to the analysis in the analysis region 43, there is cell material of type B on the conducting path. Through the surface-wave impulse of interdigital transducer 31, these cells are driven in the direction of reservoir 45 and do not reach reservoir 47. If it is observed in the analysis region 43 that there are only A cells on the conducting path 15—that is, no fluorescent signal is measured under illumination—then no surface-wave impulse is generated in direction 37 and the matter is moved in the direction of reservoir 47. Thus a separation between A and B cells can be achieved.

Obviously, other separation criteria can also be used.

The embodiment of FIG. 3 thus represents an externally controllable valve for directing the transport or for interrupting the transport in region 47.

Figure 4:
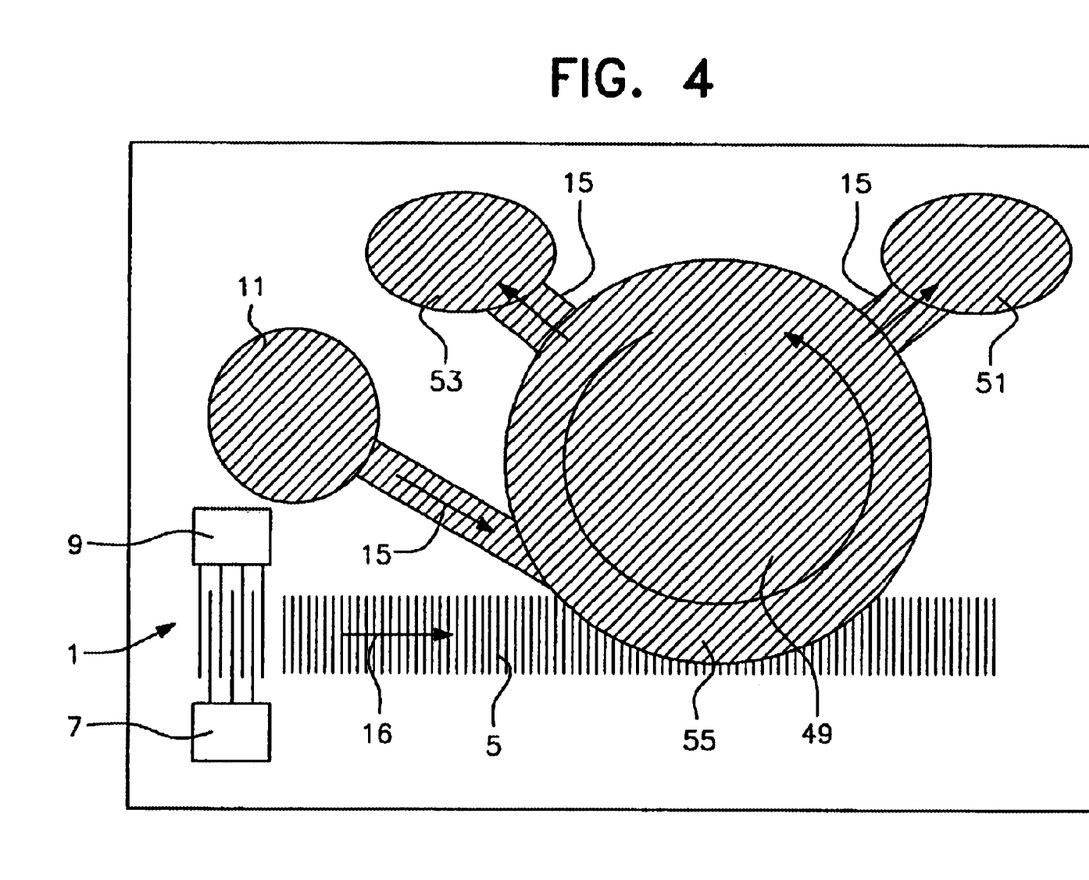
FIG. 4 shows a top view of a fourth embodiment of a device according to the invention, in a schematic representation.

FIG. 4 shows an embodiment that can be used as a centrifuge.

A round region 49 is again design by modulation of its wetting properties in such a way that, in contrast to the untreated solid-body surface, the quantity of matter to be manipulated stays there preferentially. The round region 49 is arranged so that a surface wave generated with the interdigital transducer 1 spreads out in the boundary region 55 of the round region 49. The direction of spreading 16 of the surface wave is thus tangential to the round region 49. At the circumference of the round region 49, additional regions 11, 53, 51 are surrounded by corresponding conducting paths, also generated e.g. by modulation of the wetting properties of the solid-body surface. In this case, region 11 serves as a supply reservoir and regions 51 and 53 as receiving reservoirs.

If a quantity of matter is brought into region 11, that part spreads into region 49. If a surface wave is then generated with the aid of interdigital transducer 1 in working direction 16 in the spreading region 5, it meets the matter in the overlapping region 55. The matter is then moved along the circumference of the round region 49 and thereby made to rotate. If the matter involves e.g. a liquid with suspended particles, then the heavier suspended particles are driven outward by centrifugal forces in the manner of a centrifuge and are captured by the reservoirs 51, 53 according to their weight.

In an embodiment not shown in the Figures, a network of conducting paths is produced by appropriated micro- or nanostructuring in the form of micro- or nanochannels. Such a network can assume the function of an artificial gel or sieve for (electro)phoresis processes, when, e.g., it is applied in a region 5 of the chip that is covered by the surface wave, where the surface wave crosses a conducting path 15 in which the matter is located. In this way, a size separation of components can take place in the manner of a sieve or an artificial gel.

Figure 5:
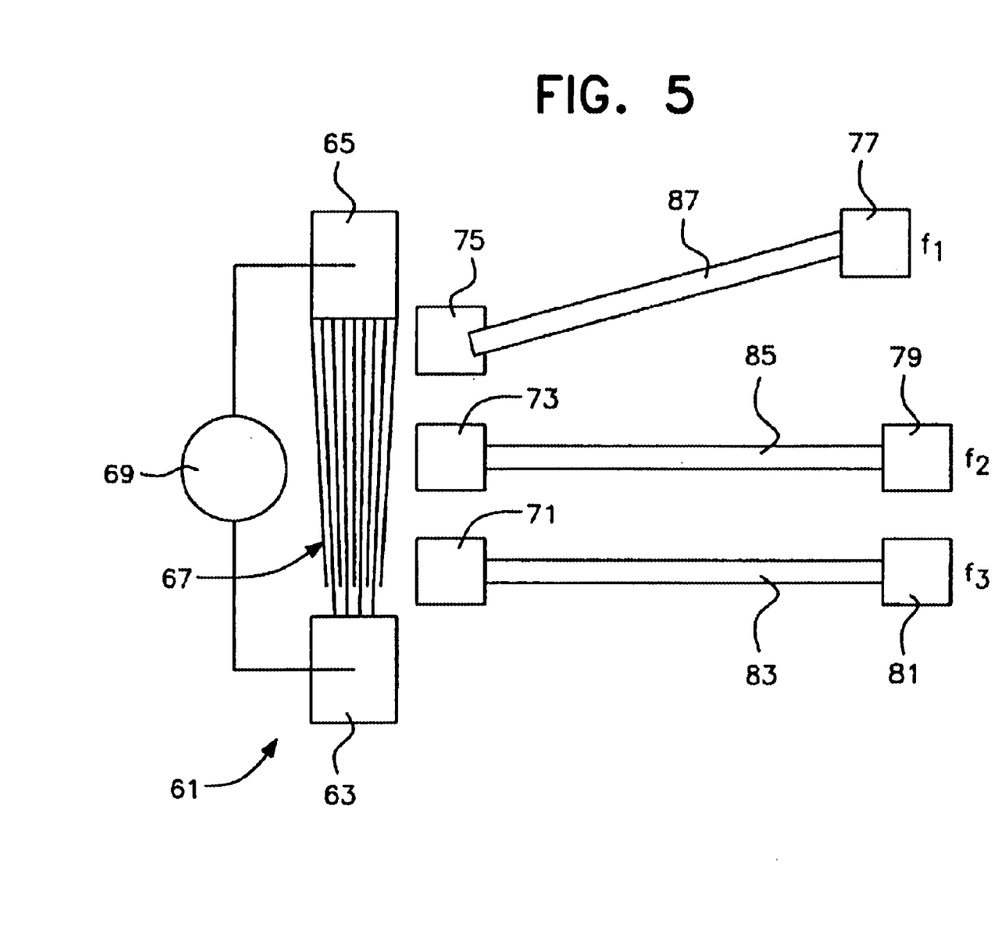
FIG. 5 shows a top view of a fifth embodiment of a device according to the invention, in a schematic representation.

FIG. 5 shows an embodiment with a so-called "tapered" interdigital transducer 61. The tapered interdigital transducer has meshing fingers 67, the distances between which decrease linearly in the example shown from one electrode 65 to another electrode 63. The method of operation of this tapered interdigital transducer will be explained with reference to FIG. 6.

Figure 6:
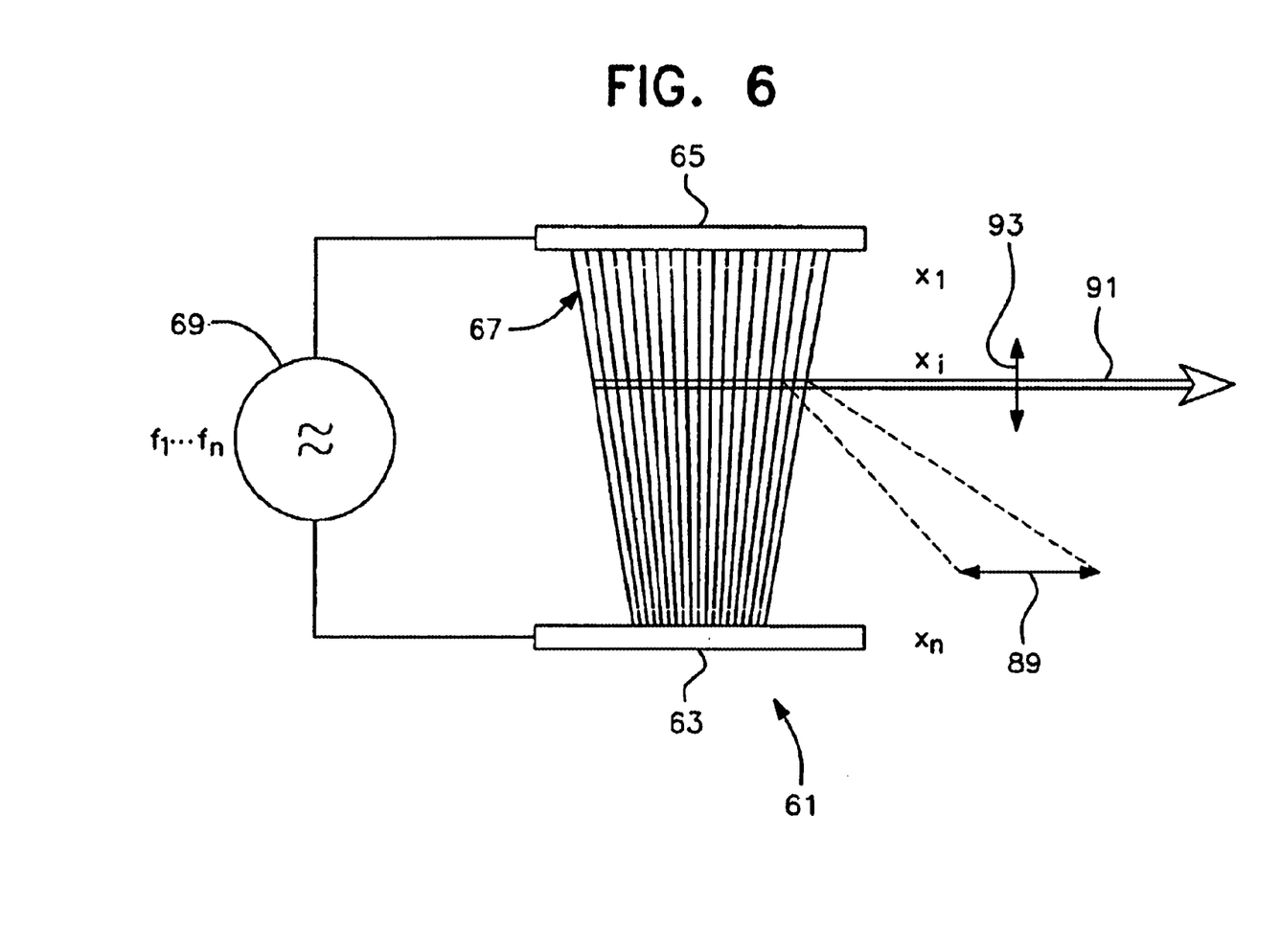
FIG. 6 shows a top view of a detail of the embodiment of FIG. 5, in a schematic representation.

The two finger-electrode structures 67, which mesh in the manner of combs, and which are connected to the electrodes 65 and 63, are represented, for example, in such a way that the spatial distance 89 between them along the axis of the interdigital transducer changes from $\lambda_0$ at position $x_0$, through $\lambda_i$ at position $x_i$, to $\lambda_n$ at position $x_n$. Since the wave length of a surface wave corresponds to the distance 89 between the individual fingers, the wavelength $\lambda_i$ with which the surface wave is generated at point $x_i$ can be determined in advance. The connection between wavelengths and the applied frequency results from $f_i = v/\lambda_i$, where v is the speed of sound on the surface. By selecting the applied frequency of $f_1$ to $f_n$ through $f_i$ with which the alternating-voltage source 69, the place $x_i$ at which the surface waves should be generated can be selected. Only there will a surface wave be generated in direction 91. By changing the frequency $f_1$ of this surface-wave beam 91 is shifted according the direction of the arrow 93 shown. In this way, a local surface wave can be generated very precisely, the spreading region of which can be set very precisely by setting the frequency.

In FIG. 5, a tapered interdigital transducer 61 of this kind is used in order to control various reservoirs 71, 73, 75. These reservoirs 71, 73, 75 are connected through conducting paths 83, 85, 87 to receiving reservoirs 81, 79, 77. If matter is found in each of the reservoirs, then by selecting the frequency applied to the interdigital transducer 61, it can be determined which quantity of matter should be given a surface-wave impulse. Only this quantity of matter will then be moved into the associated receiving reservoir. If, e.g., a lower frequency is applied, then the interdigital transducer is in resonance in the region in which the individual fingers are farther from each other, and the matter is moved from reservoir 75 by an impulse transfer from the surface wave along the conducting path 87 to reservoir 77. When a higher frequency is applied, the interdigital transducer is in resonance at a point at which the individual fingers lie closer together. For example, if the only quantity of matter located in reservoir 71 is encountered by the impulse of the surface wave, only it moves along trajectory 83 into reservoir 81. With such an embodiment, specific control of particular quantities of matter is possible.

If a quantity of matter is applied to all of regions 71, 73, and 75, then by specific locally determined irradiation of a surface wave of appropriate frequency, a particular one of these regions can be controlled in order to divide the quantity of matter.

In contrast to tapered interdigital transducers, so-called focusing interdigital transducers can also be provided, in which the distances between the fingers changes along the axis of the converter digitally, i.e. stepwise, in order to select certain regions of the surface to be covered with the surface wave, depending on the applied frequency.

In the embodiments presented so far, a specially prepared conducting path is provided on the chip surface. If, however, the quantity of matter is to move precisely in the direction of the spreading direction of a surface wave, such preparation is not necessary, since the quantity of matter is held together, as a rule, by its surface tension.

The quantity of matter then moves along the impulse or the sum of impulses, when several surface waves are sent to the quantity of matter. Such an embodiment as the advantage that the movement of the quantity of matter is not restricted to a particular conducting surface, but the movement can be controlled in its direction by an appropriate arrangement of the interdigital transducer or by controlling the individual interdigital transducers.

Figure 7:
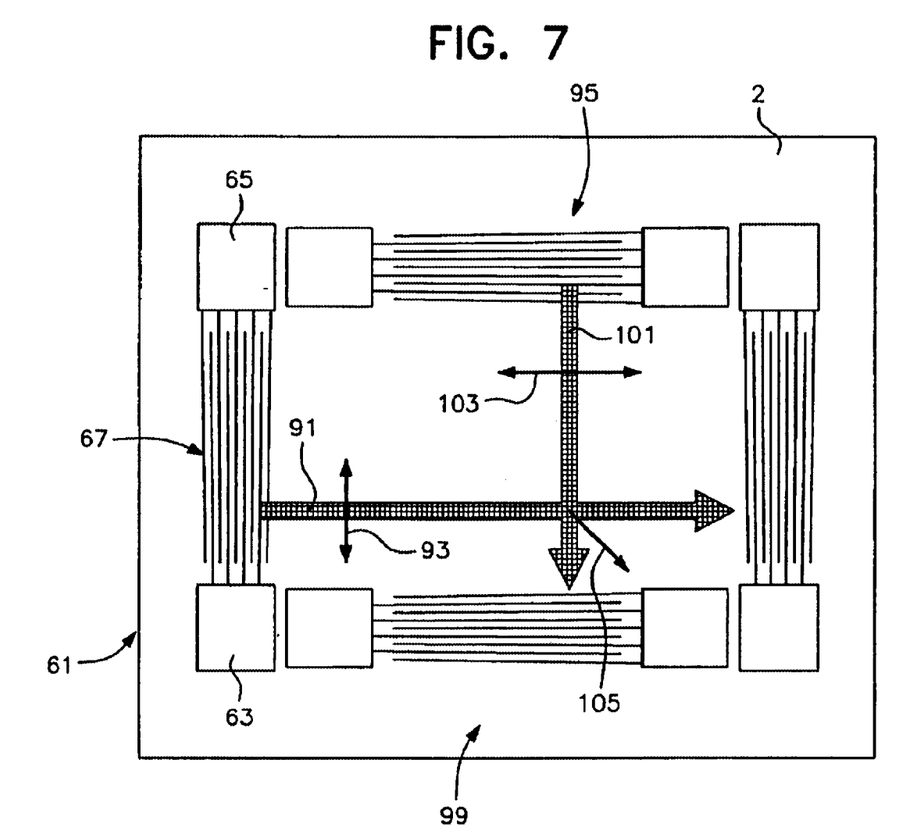
FIG. 7 shows a sixth embodiment of a device according to the invention, in a schematic representation.

This is indicated schematically in FIG. 7. Four interdigital transducers 61, 95, 97, and 99 are shown. As an example of the four interdigital transducers, the fingers 67 and the electrodes 65 and 63 of the first transducer 61 are indicated. The interdigital transducers are again constructed as tapered transducers. In the example shown, the first interdigital transducer 61 generates a surface wave in direction 91. By selecting the frequency, as has been described with reference to FIG. 6, it can be achieved that the region covered by the surface wave changes along arrow 93. In a similar way, the second interdigital transducer 95 acts to generate a surface wave in region 101. Changing the input frequency shifts the spreading region of the surface wave to direction 103. A quantity of matter located at the crossing point of the spreading region is subjected to the entire impulse of the surface wave in direction 105. By an appropriate selection of the spreading region and selection of the position of the spreading region by setting the frequencies on the various transducers 67 and 95, the impulse direction 105 can be set freely. In this case, the amplitude of the individual surface wave can be determined by means of the amplitude of the interdigital surface waves through the amplitude of the applied alternating-voltage signal, so that the angle of the resulting impulse 105 can also be changed.

By applying an alternating voltage to interdigital transducers 97 and 99, a movement can be generated in the other direction.

Obviously, other geometries of interdigital transducers can be selected in order to be able to generate movements in desired directions.

If the individual interdigital transducers on the chip 2 are designed in such a way that they do not cover the range of resonance frequencies and the individual interdigital transducers are connected in parallel, then the interdigital transducer that should generate a surface wave can be selected with the aid of the applied frequency. Thus an individual interdigital transducer can be selected in a simple manner by applying a particular frequency.

The individual embodiments also permit wireless remote control. Irradiation of an appropriate frequency onto the individual transducers makes the wireless control and generation of the associated surface waves possible. In addition, the individual transducers can be provided with a corresponding antenna device. In an embodiment in which the individual transducers do not have the same resonance frequency, it can be decided through simple selection of the irradiated frequency, without a wire, which particular transducer should generate a surface wave and be sent to a quantity of matter.

In such an embodiment, e.g., the high-frequency source 69 of FIGS. 6 and 5 is replaced by an antenna.

Obviously, any combinations of the individual embodiments can be conceived on a chip, in order to be able to perform various processes. Devices according to the invention can also be combined with corresponding analysis station. It is especially advantageous that such analysis stations be produced directly on semiconductor substrates simultaneously and in an integrated manner, and therefore simply and cost-favorably. Light sources, such semiconductor laser diodes, and optical detectors for fluorescence analysis, process for measuring electric and dielectric properties of the matter to be transported the mass and size distribution of quantities of matter should be mentioned here especially. Through miniaturized heaters or regions with electric fields that can be set statically, etc., a wide field of possible applications is opened that can extend from physics through chemistry to biology and gene technology. The processes according to the invention and the device according to the invention make it possible to move, position, and isolate the smallest quantities of matter specifically on the surface of a solid body. With this, under certain circumstances, several different quantities of matter can be moved separately from one another, independently. A possible application would thus be, e.g., a physical-chemical reaction of two or more components of the smallest quantities of materials at a predetermined site on the solid body. Thus applications in nano- or femtochemistry are possible. Also solid materials, such as e.g. clusters or the smallest quantities of one or more chemical reagents or similar substances can be moved specifically on the surface of a solid body. With this, we are also in a position to define the position and pattern of the smallest amounts of solid substances on the surface.

Precisely a combination with additional analysis stations that are generated on the same solid-body material makes possible many embodiments that serve as a whole as "kits" for a "lab on the chip." The modular construction of such a "lab on a chip" also permits the properties of the overall system to be simulated by linking the corresponding characteristics of the individual elements by means of suitable software.

Through the simple manner of construction with known planar technologies, cost-favorable production and user-specific design can also be achieved easily.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A process for specific and direct manipulation of small quantities of matter on a solid-body surface,
   which comprises generating, with the aid of one or more acoustic surface waves generated by a surface-wave generator, an impulse along the solid-body surface,
   which interacts with at least one quantity of matter in order to cause movement of said quantity of matter on said surface in a first direction, said functionalization being achieved by modulation of wetting properties of parts of said solid-body surface to define at least one hydrophobic region and at least one region that is hydrophilic as compared with said hydrophobic region, or at least one lipophobic region and at least one region that is lipophilic as compared with said lipophobic region.

2. The process according to claim 1, in which, by functionalizing parts of the solid-body surface, at least one trajectory is defined, said at least one quantity of matter being moved by said impulse along said at least one trajectory.

3. The process according to claim 2, in which the functionalization of the solid-body surface is further achieved by grooves, or barriers.

4. The process according to claim 1, in which said at least one hydrophobic region and at least one region that is hydrophilic in comparison to it or at least one lipophobic region and at least one region that is lipophilic in comparison to it are defined lithographically.

5. The process according to claim 1, in which the functionalization of the solid-body surface by modulation of the wetting properties of parts of the solid-body surface is achieved through silanization of said parts of the solid-body surface.

6. The process according to claim 1, in which the acoustic surface waves are generated by electric stimulation.

7. The process according to claim 1, in which interdigital converters are used to generate the acoustic surface waves.

8. The process according to claim 6, in which the acoustic surface waves are generated by means of the piezoelectric effect in a piezoelectric substrate or a piezoelectric region of a substrate.

9. The process according to claim 8, in which a piezoelectric layer is used on the substrate surface to generate the surface waves, said layer having different wetting properties than a remainder of the substrate surface.

10. The process according to claim 1, in which the impulse transfer between the at least one acoustic surface wave and the at least one quantity of matter is transmitted by the electric fields accompanying the wave in a piezoelectric substrate or at least in a piezoelectric region of the solid-body surface.

11. The process according to claim 1, in which the impulse transfer between the at least one acoustic wave and the at least one quantity of matter is transmitted by the mechanical deformation of the solid-body surface that accompanies the surface wave.

12. The process according to claim 1, in which shear waves, Lamb waves, Rayleigh waves, Love waves, or combinations thereof are used as surface waves.

13. The process according to claim 1, in which surface waves of different frequencies are sent to different regions of the surface.

14. The process according to claim 13, in which, to generate surface waves in different regions of the surface, at least two generators with different operating frequencies are used for surface waves.

15. The process according to claim 14, in which the at least two generators include interdigital converters with constant but different distances between the fingers of each.

16. The process according to claim 7, in which, to generate surface waves of different frequencies, at least one interdigital converter with non-constant distances between the fingers is used.

17. The process according to claim 1, in which superimposition of at least two acoustic surface waves is used to establish a size and direction of a velocity vector of the at least one quantity of matter.

18. The process according to claim 1, in which the at least one quantity of matter is divided by at least one acoustic surface wave into at least two smaller subquantities.

19. The process according to claim 1, in which the at least one quantity of matter is analyzed within at least one region of the solid-body surface in regard to at least one physical, chemical, or biological characteristic.

20. The process according to claim 19, in which a part of the at least one quantity of matter is separated from the rest of the quantity of matter, either before or after the analysis.

21. The process according to claim 19, in which the at least one quantity of matter is analyzed with at least one acoustic surface wave in regard to a size, mass, and optical, magnetic, electric, and/or dielectric properties of said at least one quantity of matter.

22. The process according to claim 1, in which at least one part of the at least one quantity of matter is modified in at least one region on the solid-body surface by chemical, physical, or biological processes.

23. The process according to claim 22, in which the at least one part of the at least one quantity of matter is modified by functionalizing at least one region of the solid-body surface with respect to its physical, chemical, or biological properties.

24. The process according to claim 19, in which the at least one quantity of matter to be analyzed is immobilized reversibly and temporarily on at least one region of the solid-body surface by modulation or coating of said at least one region of the solid-body surface through chemisorption or physisorption.

25. The process according to claim 1, in which at least two quantities of material are brought into contact in at least one region of the solid-body surface by specific and direct movement for purposes of being mixed and/or at least one physical, chemical, or biological reaction.

26. The process according to claim 25, in which the at least two quantities of matter are moved toward each other with the aid of two surface waves running in opposite directions.

27. The process according to claim 1, in which surface waves are sent from various directions to the at least one quantity of matter, in order to achieve a mixing of the at least one quantity of matter.

28. The process according to claim 1, in which the at least one surface wave is generated by wireless irradiation of at least one electromagnetic wave into at least one generator for surface waves.

29. The process according to claim 1, in which at least one additional surface wave is irradiated from a second direction onto the at least one quantity of matter that does not correspond to the first direction of movement of the quantity of matter.

30. The process according to claim 1, in which at least one surface wave is sent approximately tangentially onto at least one quantity of matter, in order to place said quantity of matter in rotation.

31. A process for specific and direct manipulation of small quantities of matter on a solid-body surface which comprises generating, with the aid of one or more acoustic surface waves generated by a surface-wave generator, an impulse along the solid-body surface which interacts with at least one quantity of matter in order to cause movement of said quantity of matter on said surface along at least one defined trajectory, said trajectory defined by the functionalization of parts of the solid-body surface through modulation of wetting properties of said solid-body surface to define at least one hydrophobic region and at least one region that is hydrophilic as compared with said hydrophobic region, or at least one lipophobic region and at least one region that is lipophilic as compared with said lipophobic region.

32. A process for specific and direct manipulation of small quantities of matter on a solid-body surface which comprises generating, with the aid of one or more acoustic surface waves generated by a surface-wave generator, an impulse along the solid-body surface which interacts with at least one quantity of matter in order to cause movement of said quantity of matter along at least one defined trajectory, said trajectory defined by the functionalization of at least one part of the solid-body surface, said functionalization being achieved by modulation of wetting properties of at least one part of said solid-body surface through silanization of said part of the solid-body surface so that said wetting properties of said part are different from surrounding solid-body surface regions.

33. A process for specific and direct manipulation of small quantities of matter on a solid-body surface comprising the steps of:
generating, one or more acoustic surface waves by electric stimulation to produce an impulse along the solid-body surface, said surface wave being generated by means of the piezoelectric effect in a piezoelectric region of said solid-body surface, said piezoelectric region having different wetting properties than the rest of the solid-body surface; and
making the impulse interact with at least one quantity of matter in order to cause movement on the surface in a desired direction.

34. The process according to claim 33, in which, by functionalizing parts of the solid-body surface, at least one defined trajectory is set for the quantity of matter and the at least one quantity of matter is moved by the impulse transfer along said at least one trajectory.

35. A process for specific and direct manipulation of small quantities of matter on a solid-body surface comprising the steps of:
generating, with the aid of one or more acoustic surface waves, an impulse along the solid-body surface, said surface waves being generated by interdigital converters, with at least one of said converters having non-constant distances between fingers thereof to generate surface waves of different frequencies; and
making the impulse interact with at least one quantity of matter in order to cause movement on the surface in a desired direction.

36. The process according to claim 35, in which, by functionalizing parts of the solid-body surface, at least one defined trajectory is set for the quantity of matter and the at least one quantity of matter is moved by the impulse transfer along this at least one trajectory.

37. The process according to claim 36, in which the functionalization of the solid-body surface is achieved by grooves, barriers, lithographic definition of channels, or modulation of wetting properties.

38. A process according to claim 37, in which the functionalization is achieved by modulation of the wetting properties of the solid-body surface by definition of at least one hydrophobic region and at least one region that is hydrophilic in comparison to said hydrophobic region or at least one lipophobic region and at least one region that is lipophilic in comparison to said lipophobic region.

39. The process according to claim 38, in which said at least one hydrophobic region and at least one region that is hydrophilic in comparison to it or at least one lipophobic region and at least one region that is lipophilic in comparison to it are defined lithographically.

40. The process according to claim 35, in which the acoustic surface waves are generated by means of the piezoelectric effect in a piezoelectric substrate or a piezoelectric region of a substrate.

41. The process according to claim 35, in which the impulse transfer between the at least one acoustic surface wave and the at least one quantity of matter is transmitted by the electric fields accompanying the wave in a piezoelectric substrate or at least in a piezoelectric region of the solid-body surface.

42. The process according to claim 35, in which the impulse transfer between the at least one acoustic wave and the at least one quantity of matter is transmitted by the mechanical deformation of the solid-body surface that accompanies the surface wave.

43. The process according to claim 35, in which shear waves, Lamb waves, Rayleigh waves, Love waves, or combinations thereof are used as surface waves.

44. The process according to claim 35, in which surface waves of different frequencies are sent to different regions of the surface.

45. The process according to claim 44, in which, to generate surface waves in different regions of the surface, at least two generators with different operating frequencies are used for surface waves.

46. The process according to claim 45, in which the at least two generators include interdigital converters with constant but different distances between the fingers of each.

47. The process according to claim 35, in which superimposition of at least two acoustic surface waves is used to establish a size and direction of a velocity vector of the at least one quantity of matter.

48. The process according to claim 35, in which the at least one quantity of matter is divided by at least one acoustic surface wave into at least two smaller subquantities.

49. The process according to claim in which the at least one quantity of matter is analyzed within at least one region of the solid-body surface in regard to at least one physical, chemical, or biological characteristic.

50. The process according to claim 49, in which a part of the at least one quantity of matter is separated from the rest of the quantity of matter, either before or after the analysis.

51. The process according to claim 49, in which the at least one quantity of matter is analyzed with at least one acoustic surface wave in regard to a size, mass, and optical, magnetic, electric, and/or dielectric properties of said at least one quantity of matter.

52. The process according to claim 35, in which at least one part of the at least one quantity of matter is modified in at least one region on the solid-body surface by chemical, physical, or biological processes.

53. The process according to claim 52, in which the at least one part of the at least one quantity of matter is modified by functionalizing at least one region of the solid-body surface with respect to its physical, chemical, or biological properties.

54. The process according to claim 49, in which the at least one quantity of matter to be analyzed is immobilized reversibly and temporarily on at least one region of the solid-body surface by modulation or coating of said at least one region of the solid-body surface through chemisorption or physisorption.

55. The process according to claim 35, in which at least two quantities of material are brought into contact in at least one region of the solid-body surface by specific and direct movement for purposes of being mixed and/or at least one physical, chemical, or biological reaction.

56. The process according to claim 55, in which the at least two quantities of matter are moved toward each other with the aid of two surface waves running in opposite directions.

57. The process according to claim 35, in which surface waves are sent from various directions to the at least one quantity of matter, in order to achieve a mixing of the at least one quantity of matter.

58. The process according to claim 35, in which the at least one surface wave is generated by wireless irradiation of at least one electromagnetic wave into at least one generator for surface waves.

59. The process according to claim 35, in which at least one additional surface wave is irradiated from a direction onto the at least one quantity of matter that does not correspond to the original direction of movement of the quantity of matter.

60. The process according to claim 35, in which at least one surface wave is sent approximately tangentially onto at least one quantity of matter, in order to place said quantity of matter in rotation.

* * * * *

UNITED STATES PATENT AND TRADEMARK OFFICE
CERTIFICATE OF CORRECTION

PATENT NO. : 6,777,245 B2 Page 1 of 1
APPLICATION NO. : 09/766677
DATED : August 17, 2004
INVENTOR(S) : Wixforth It is certified that error appears in the above-identified patent and that said Letters Patent is hereby corrected as shown below:

Col. 15 lines 28-29
Delete "said functionalization being" and replace with --wherein functionalization of the solid body surface is--.

Signed and Sealed this

Twenty-ninth Day of April, 2008

JON W. DUDAS
*Director of the United States Patent and Trademark Office*